United States Patent
Keith-Lucas et al.

(10) Patent No.: US 9,655,764 B2
(45) Date of Patent: May 23, 2017

(54) SURGICAL FOOT SUPPORT WITH HANDLES

(75) Inventors: Darwin Keith-Lucas, Arlington, MA (US); Orlando Soto, Salem, MA (US); David E. Chella, Brighton, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 1274 days.

(21) Appl. No.: 13/151,617

(22) Filed: Jun. 2, 2011

(65) Prior Publication Data

US 2012/0305005 A1    Dec. 6, 2012

(51) Int. Cl.
A61G 15/00 (2006.01)
A61F 5/37 (2006.01)
A61G 13/12 (2006.01)
A61G 13/00 (2006.01)

(52) U.S. Cl.
CPC ........ A61F 5/3761 (2013.01); A61G 13/0063 (2016.11); A61G 13/0081 (2016.11); A61G 13/125 (2013.01)

(58) Field of Classification Search
CPC .............. A61B 17/0206; A61B 17/025; A61B 17/3423; A61B 17/3476; A61B 2017/349; A61B 90/50; A61B 34/25; A61B 17/00234; A61B 17/064; A61B 17/2812; A61B 17/285; A61B 17/320068; A61B 17/320092
USPC .... 602/23, 27, 28, 29, 60–66; 128/869, 882; 623/27–29, 47; 2/22
See application file for complete search history.

(56) References Cited

U.S. PATENT DOCUMENTS

| | | |
|---|---|---|
| 542,390 A | 7/1895 | Linn |
| 2,267,924 A | 12/1941 | Johnston |
| 2,609,261 A | 9/1952 | Parker |
| 2,630,288 A | 3/1953 | Eubanks, Sr. |
| 2,732,269 A | 1/1956 | Astroff |
| 2,801,142 A | 7/1957 | Adams |
| 2,910,061 A | 10/1959 | Rabjohn |
| 3,226,105 A | 12/1965 | Weickgenannt et al. |
| 3,540,719 A | 11/1970 | Romney et al. |
| 3,762,514 A | 10/1973 | Freitag |
| 3,845,945 A | 11/1974 | Lawley et al. |
| 3,982,742 A | 9/1976 | Ford |
| 4,054,282 A | 10/1977 | Hamer |
| 4,163,536 A | 8/1979 | Heller et al. |
| 4,180,254 A | 12/1979 | Lee et al. |
| 4,185,813 A | 1/1980 | Spann |
| 4,221,370 A | 9/1980 | Redwine |
| 4,252,306 A | 2/1981 | Johnson et al. |

(Continued)

FOREIGN PATENT DOCUMENTS

ES    1071618    * 3/2010

OTHER PUBLICATIONS

"Peace of Mind? Piece of Cake!, Great Products . . . Great Prices" O.R. Direct Surgical Table Accessories, Fall 1999, (24 pages).

(Continued)

Primary Examiner — Michael Brown
(74) Attorney, Agent, or Firm — Barnes & Thornburg, LLP

(57) ABSTRACT

A surgical boot includes a shell shaped to receive a patient's foot. The shell has a plurality of handles molded integrally with a main body. The handles are sized and arranged for gripping by a surgeon during surgery to reposition the foot.

22 Claims, 5 Drawing Sheets

(56) References Cited

U.S. PATENT DOCUMENTS

| | | |
|---|---|---|
| 4,323,060 A | 4/1982 | Pecheux |
| 4,367,869 A | 1/1983 | Dailey et al. |
| 4,373,709 A | 2/1983 | Whitt |
| 4,407,277 A | 10/1983 | Ellison |
| 4,418,900 A | 12/1983 | Ricke |
| 4,426,071 A | 1/1984 | Klevstad |
| 4,428,571 A | 1/1984 | Sugarman |
| 4,443,005 A | 4/1984 | Sugarman et al. |
| 4,471,952 A | 9/1984 | Spann |
| 4,482,138 A | 11/1984 | Spann |
| 4,526,355 A | 7/1985 | Moore et al. |
| 4,545,573 A | 10/1985 | Murphy |
| 4,564,164 A | 1/1986 | Allen et al. |
| 4,564,180 A | 1/1986 | Agee et al. |
| 4,577,730 A | 3/1986 | Porter |
| 4,579,324 A | 4/1986 | McConnell |
| 4,620,698 A | 11/1986 | Reed et al. |
| 4,632,349 A | 12/1986 | Anstey |
| 4,681,309 A | 7/1987 | Lechner |
| 4,698,837 A | 10/1987 | Van Steenburg |
| 4,702,465 A | 10/1987 | McConnell |
| 4,730,609 A | 3/1988 | McConnell |
| 4,732,145 A | 3/1988 | Latham |
| 4,766,892 A | 8/1988 | Kreitman |
| 4,782,827 A | 11/1988 | Paratte |
| 4,802,464 A | 2/1989 | Deprez |
| 4,807,618 A | 2/1989 | Auchinleck et al. |
| 4,809,687 A | 3/1989 | Allen |
| 4,827,496 A | 5/1989 | Cheney |
| 4,840,363 A | 6/1989 | McConnell |
| 4,886,258 A | 12/1989 | Scott |
| 4,898,491 A | 2/1990 | Van Steenburg |
| 4,909,264 A | 3/1990 | Wadsworth, III et al. |
| 4,913,413 A | 4/1990 | Raab |
| 4,940,218 A | 7/1990 | Akcelrod |
| 5,001,739 A | 3/1991 | Fischer |
| 5,010,900 A | 4/1991 | Auchinleck et al. |
| 5,020,525 A | 6/1991 | Ewing et al. |
| 5,027,799 A | 7/1991 | Laico et al. |
| 5,042,508 A | 8/1991 | Richard |
| 5,056,535 A | 10/1991 | Bonnell |
| 5,097,847 A | 3/1992 | Mikhail et al. |
| 5,104,363 A | 4/1992 | Shi |
| 5,116,008 A | 5/1992 | Allen |
| 5,290,220 A | 3/1994 | Guhl |
| 5,291,903 A | 3/1994 | Reeves |
| 5,369,827 A | 12/1994 | Parke et al. |
| 5,410,769 A | 5/1995 | Waterman |
| 5,462,551 A | 10/1995 | Bailey et al. |
| 5,472,412 A | 12/1995 | Knoth |
| 5,481,770 A | 1/1996 | Ahlsten |
| 5,514,143 A | 5/1996 | Bonutti et al. |
| 5,515,562 A | 5/1996 | Miller et al. |
| 5,560,577 A | 10/1996 | Keselman |
| 5,582,379 A | 12/1996 | Keselman et al. |
| 5,608,934 A | 3/1997 | Torrie et al. |
| 5,636,899 A | 6/1997 | Schiff et al. |
| 5,645,079 A | 7/1997 | Zahiri et al. |
| 5,738,675 A | 4/1998 | Botimer |
| 5,758,374 A | 6/1998 | Ronci |
| 5,799,349 A | 9/1998 | Petersen |
| 5,802,641 A | 9/1998 | Van Steenburg |
| 5,806,117 A | 9/1998 | Gotfried |
| 5,918,330 A | 7/1999 | Navarro et al. |
| 5,961,085 A | 10/1999 | Navarro et al. |
| 6,058,534 A | 5/2000 | Navarro et al. |
| 6,108,841 A | 8/2000 | Cameron et al. |
| 6,195,820 B1 | 3/2001 | Heimbrock et al. |
| 6,263,531 B1 | 7/2001 | Navarro et al. |
| 6,289,537 B1 | 9/2001 | Hopper et al. |
| 6,289,558 B1 | 9/2001 | Hammerslag |
| 6,336,412 B2 | 1/2002 | Heimbrock et al. |
| 6,467,487 B1 | 10/2002 | Rios |
| 6,629,944 B2 | 10/2003 | Smart |
| 6,663,055 B2 | 12/2003 | Boucher et al. |
| 6,704,959 B2 | 3/2004 | Schuerch |
| 6,811,541 B2 | 11/2004 | Lambert |
| 6,874,184 B2 | 4/2005 | Chandler |
| 7,018,352 B2 * | 3/2006 | Pressman et al. .............. 602/27 |
| 7,243,654 B2 | 7/2007 | Schuerch |
| 7,281,341 B2 * | 10/2007 | Reagan et al. ................. 36/50.1 |
| 7,316,040 B2 | 1/2008 | Siccardi et al. |
| 7,337,483 B2 | 3/2008 | Boucher et al. |
| 7,591,050 B2 | 9/2009 | Hammerslag |
| RE41,412 E | 7/2010 | Van Steenburg |
| 7,832,401 B2 | 11/2010 | Torrie et al. |
| 7,870,624 B1 | 1/2011 | Winston |
| 2005/0160533 A1 | 7/2005 | Boucher et al. |
| 2006/0225743 A1 | 10/2006 | Schuerch |
| 2007/0265635 A1 | 11/2007 | Torrie et al. |
| 2009/0235457 A1 | 9/2009 | Harvey |
| 2010/0242181 A1 | 9/2010 | Bochiner et al. |
| 2011/0009791 A1 * | 1/2011 | Hopmann ....................... 602/23 |
| 2011/0023893 A1 | 2/2011 | Striggow et al. |
| 2011/0197362 A1 | 8/2011 | Chella et al. |
| 2011/0306903 A1 * | 12/2011 | Crabtree et al. .............. 600/595 |

OTHER PUBLICATIONS

"Passionate About Positioning", Allen Medical Systems, (20 pages) 1998.

U.S. Appl. No. 61/354,060, "Knee Ligament Testing Device for Measuring Drawer and Rotational Laxity", by Stephanie Crabtree et al, filed Jun. 11, 2010, 13 pages.

* cited by examiner

SURGICAL FOOT SUPPORT WITH HANDLES

BACKGROUND

The present disclosure relates to a patient support apparatus for supporting a patient during surgery. More particularly, the present disclosure relates to a surgical boot for supporting a patient during surgery.

Often, when a patient is sedated for a surgery, the patient is supported by and secured to braces or supports coupled to a surgical table. Sometimes, unique supports are provided for a patient's extremities such as arm boards, leg supports, hand boards, stirrups, and boots.

Supports known in the art are sometimes adjusted by cranks, motors, or other mechanical drivers. Such supports can be expensive to produce or difficult to operate.

SUMMARY

A surgical boot has one or more of the features recited in the appended claims and/or the following features which, alone or in any combination, may comprise patentable subject matter:

A surgical boot may include a shell shaped to receive a patient's foot. The shell may have a plurality of handles molded integrally with the main body. The handles may be sized and arranged for gripping by a surgeon during surgery to reposition the foot.

In some embodiments, the plurality of handles may form a plurality of handhold openings extending through the shell. The shell may have a substantially uniform thickness. The plurality of handles may be arcuate.

The surgical boot may also include a securing system having a foot securing system configured to couple a patient's foot to the shell and a calf securing system configured to couple a patient's leg to the shell. It is contemplated that the foot securing system may include a toe strap assembly coupled to the shell and configured to extend over a patient's foot near a toe end of the shell. The calf securing system may include a calf strap assembly coupled to the shell and configured to extend over a patient's leg near a heel end of the shell. The foot securing system may also include a main strap assembly and a heel strap assembly. The main strap assembly may be configured to extend over a patient's foot. The heel strap may be coupled to the main strap assembly and may be configured to extend around a patient's heel.

In some embodiments, the surgical boot may further include a coupler configured to couple the surgical boot to a surgical support. The shell may include a sole and the coupler may extend down from the sole of the shell.

According to this disclosure, a surgical boot may include a shell, a foot portion, and a calf portion. The shell may include a sole having a heel end and a toe end, a foot portion having a pair of sidewalls coupled to the sole, and a calf portion coupled to and extending above the foot portion. The foot portion may include a pair of lower handles forming a pair of handhold spaces between the sole and the pair of handles. The pair of handhold spaces may be situated between the heel end and the toe end of the sole.

In some embodiments, the calf portion includes a calf support and a pair of upper handles extending along the calf support and forming a pair of handhold spaces between the pair of upper handles and the calf support. The handhold spaces of the upper handholds and the handhold spaces of the lower handholds may extend through the boot shell.

It is contemplated that the surgical boot may include a securing system including a foot securing system adapted to secure a patient's foot to the sole and a calf securing system adapted to secure a patient's calf to the calf portion. The foot securing system may include a main strap assembly and a toe strap assembly. The main strap assembly may extend from a right side to a left side of the sole near the heel end of the sole. The toe strap assembly may be coupled to the sole and may extend from a right side to a left side of the sole near the toe end of the sole. The foot securing system may include a heel strap assembly having a heel strap coupled to the main strap assembly and a heel pad.

According to this disclosure, a surgical boot may include an integrally formed shell including a sole, a foot portion, a calf portion, and a first pair of handles. The sole may include a toe end and a heel end. The foot portion may be coupled to and may extend up from the sole. The calf portion may be situated above the foot portion at the heel end of the sole. The first pair of handles may be situated above the sole. The pair of handles may also form a first pair of handhold openings on opposing sides of the shell.

The boot shell may also include a second pair of handles situated above the sole. The second pair of handles may form a second pair of handhold openings on opposing sides of the shell.

It is contemplated that the surgical boot may further include a securing system. The securing system may include a foot securing system adapted to secure a patient's foot to the sole and a calf securing system adapted to secure a patient's calf to the calf portion. The securing system may be situated between the first pair of handles.

In some embodiments, the surgical boot may also include a coupler. The coupler may extend downwardly from the sole and may be configured to couple to a surgical support.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
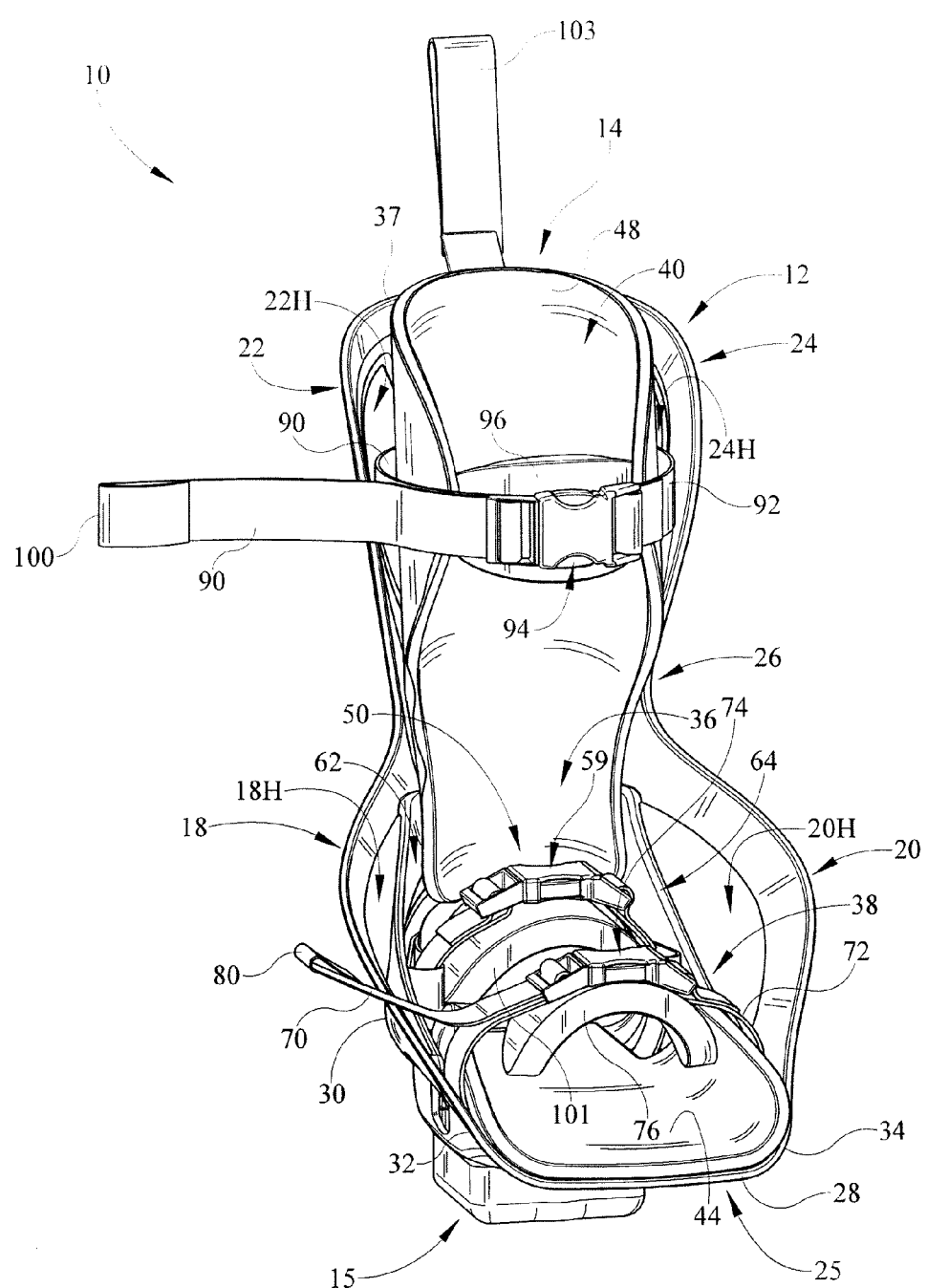
FIG. 1 is a front perspective view of a surgical boot including a shell and a securing system showing that the shell forms a plurality of handles for use by a surgeon during surgery to reposition a patient's foot and that the securing system is configured to couple a patient's foot to the shell.

In one illustrative embodiment, a surgical foot support is embodied as a surgical boot 10 including a shell 12 providing supporting structure for the surgical boot 10, a securing system 14 for coupling a patient to the shell 12 of the surgical boot 10, and a quick disconnect receiver 15 for coupling surgical boot 10 to another surgical support as shown in FIG. 1. The shell 12 includes a main body 16 and a plurality of handles 18, 20, 22, 24 coupled to main body 16. Each of the plurality of handles 18, 20, 22, 24 is sized and arranged for gripping by a surgeon during surgery to reposition a patient's foot and/or leg, for example when a surgeon is distracting a patient's hip joint or performing surgery on the patient's leg.

Main body 16 of shell 12 includes a sole 25 configured to underlie a patient's foot and a calf support 26 configured to support the lower leg of a patient as suggested in FIG. 1. Sole 25 has a toe end 28, a heel end 30, a left side 32, and a right side 34. Main body 16 of shell 12 forms an upwardly-facing channel 36 that opens from the toe end 28 of the sole 25 to the heel end 30 of the sole 25 as shown, for example, in FIG. 1. A patient's foot may be lowered into upwardly-facing channel 36 of surgical boot 10 without bending the patient's foot relative to the lower leg of the patient. Calf support 26 is coupled to sole 25 and extends up above heel end 30 of sole 25.

Plurality of handles 18, 20, 22, 24 is made up of lower left handle 18, lower right handle 20, upper left handle 22, and upper right handle 24 as shown in FIG. 1. In the illustrative embodiment, shell 12 is made from a monolithic plastics material and thus each of the plurality of handles 18, 20, 22, 24 is integrally formed with main body 16 of shell 12. Illustratively, shell 12 may be made from an ABS polycarbonate blended material. Further, the plurality of handles 18, 20, 22, 24 have a thickness similar to a thickness of main body 16 as shown in FIG. 1. Illustratively, the handles 18, 20, 22, 24 and the main body 16 have a thickness of about 0.2 inches. In other embodiments, other thicknesses of shell 12 may be used.

Figure 2:
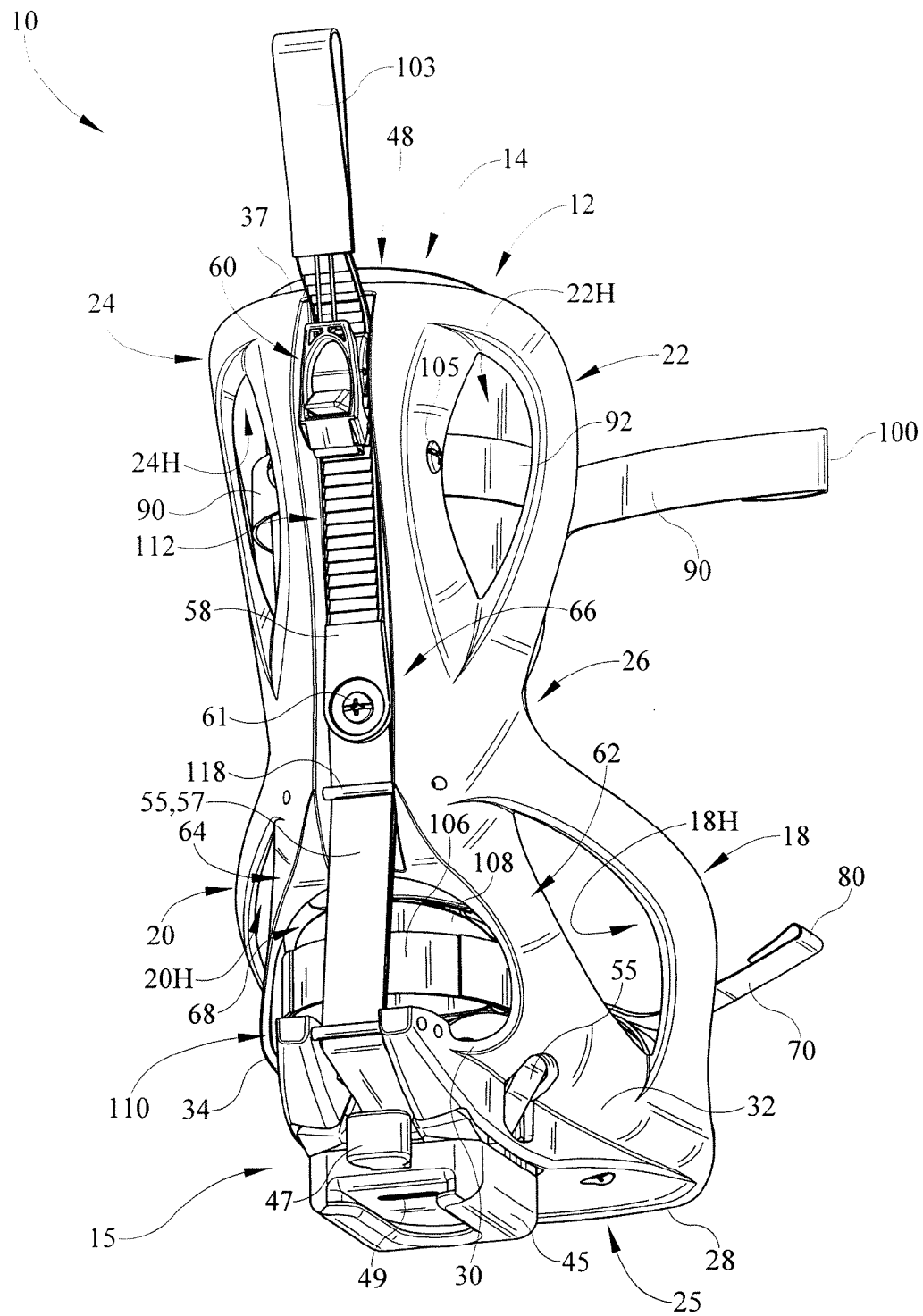
FIG. 2 is rear perspective view of the surgical boot of FIG. 1 showing a quick disconnect receiver extending down from the boot shell, the quick disconnect receiver configured to couple to a coupler and a surgical table as shown diagrammatically in FIG. 4.

Lower left handle 18 and lower right handle 20 extend from calf support 26 near heel end 30 of sole 25 to sole 25 near toe end 28 of sole 25 so that lower left and lower right handles 18, 20 are arranged to extend along the length of a patient's foot as suggested in FIG. 2. Lower left handle 18 and lower right handle 20 form corresponding lower handhold openings 18H, 20H that extend through shell 12. Lower handhold openings 18H, 20H are sized to allow a surgeon's hand to pass through shell 12. Lower left handle 18 and lower right handle 20 are arcuate and extend away from channel 36 of main body 16 along left side 32 of sole 25 and right side 34 of sole 25, respectively, so that a surgeon can grip lower left handle 18 and lower right handle 20 with a portion of his hand situated between a patient's foot and shell 12.

Upper left handle 22 and upper right handle 24 are arcuate and extend away from channel 36 along calf support 26 from a top end 37 of calf support 26 down toward sole 25 of shell 12 so that upper left and upper right handles 22, 24 are arranged to extend along the length of a patient's lower leg as suggested in FIG. 1. Upper left handle 22 and upper right handle 24 form corresponding handhold openings 22H and 24H that extend through shell 12. Upper handhold openings 22H, 24H are sized to allow a surgeon's hand to pass through shell 12. Upper left handle 22 and upper right handle 24 are arcuate and extend away from channel 36 of main body 16 along left side 32 of sole 25 and right side 34 of sole 25, respectively, so that a surgeon can grip upper left handle 22 and upper right handle 24 with a portion of his hand situated between a patient's lower leg and shell 12.

Figure 3:
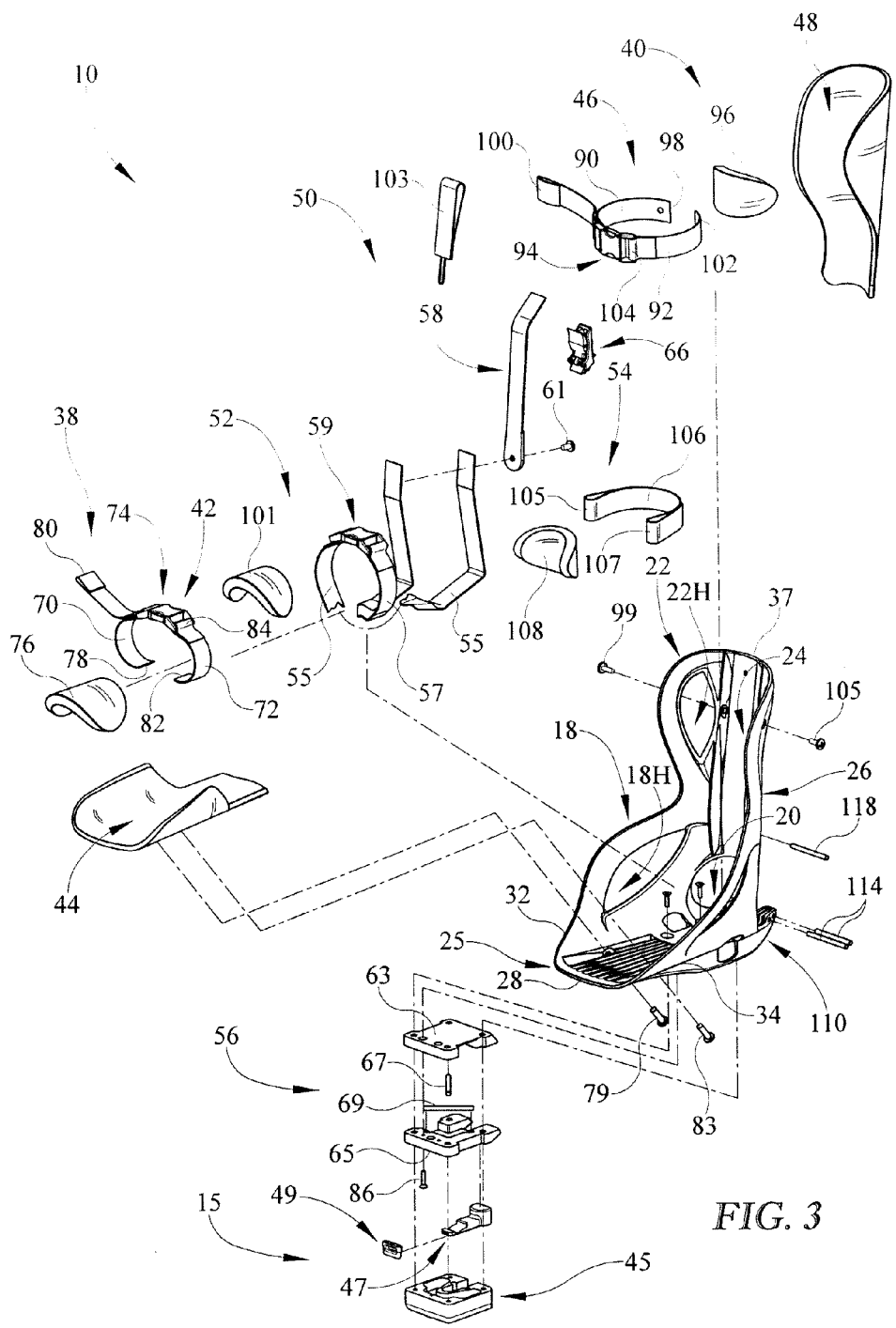
FIG. 3 is an exploded view of the surgical boot of FIG. 1 showing that the shell is integrally formed and that the securing system include a plurality of pads and straps.

Securing system 14 is configured to couple a patient's foot and lower leg to shell 12 of the surgical boot 10 and includes a foot securing system 38 and a calf securing system 40 as shown in FIG. 1. Foot securing system 38 is configured to couple a patient's foot to sole 25 of shell 12 and illustratively includes a toe strap assembly 42 and a sole pad 44 as shown in FIGS. 1 and 3. Sole pad 44 is coupled to sole 25 of shell 12 to cushion a patient's foot when a patient is secured to surgical boot 10 as suggested in FIG. 1. Calf securing system 40 is configured to couple a patient's lower leg to calf support 26 of shell 12 and illustratively includes leg strap assembly 46 and a calf pad 48 as shown in FIGS. 1 and 3. Calf pad 48 is coupled to calf support 26 of shell 12 to cushion a patient's lower leg when a patient is secured to surgical boot 10 as suggested in FIG. 1.

Figure 4:
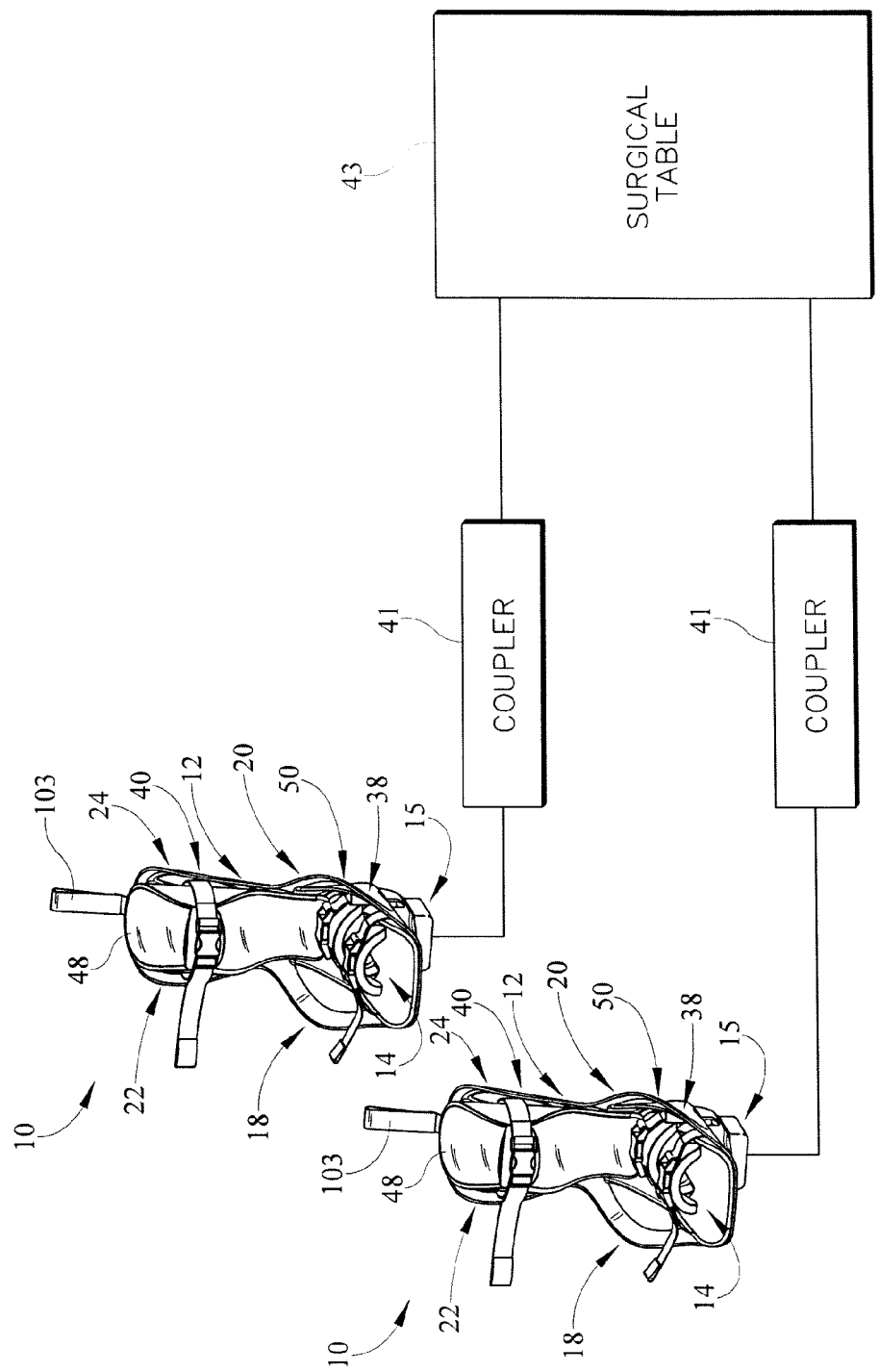
FIG. 4 is a partially diagrammatic view of a surgical table with a pair of couplers each secured to a surgical boot suggesting that the surgical boot is configured for use in a surgical setting and adapted to be supported by a surgical table.

Quick disconnect receiver 15 is illustratively coupled to a bottom side 39 of sole 25 and extends downwardly from sole 25 as shown in FIG. 2. Quick disconnect receiver 15 is configured to couple to a coupler 41 attached to a surgical table 43 as shown diagrammatically in FIG. 4. In the illustrative embodiment, quick disconnect receiver 15 includes a receiver body 45, a release handle 47, and a retainer lug 49 as shown, for example, in FIG. 3. Retainer lug 49 is configured to engage coupler 41 when quick disconnect receiver 15 is coupled to coupler 41. Release handle 47 is configured to disengage retainer lug 49 from coupler 41 so that surgical boot 10 can be moved away from coupler 41.

Coupler 41 may include one or more of a handle, a post, a spar, a clamp, and a carriage as is known in the art. In some embodiments, quick disconnect receiver 15 may be movably coupled to coupler 41 so that a caregiver can position surgical boot 10 at different positions along coupler 41. In some embodiments, quick disconnect receiver 15 may be configured to couple directly to surgical table 43. Quick disconnect receiver 15 allows surgical boot 10 to be positioned for surgery, traction, and other applications of the surgical boot 10.

In the illustrative embodiment, surgical boot 10 further includes an tightener system 50 configured to resist the movement of a patient's foot out of the surgical boot 10 when a surgeon moves surgical boot 10 to reposition a patient's foot or leg as shown in FIGS. 1-3. Tightener system 50 includes a main strap assembly 52, a heel strap assembly 54, a belt guide assembly 56, a toothed belt 58, a ratchet 60, and a handle 103 shown, for example, in FIG. 3. Main strap assembly 52 extends across a patient's foot from left side 32 of sole 25 to right side 34 of sole 25 as suggested in FIG. 1. Heel strap assembly 54 is coupled to main strap assembly 52 and extends around a patient's heel above a patient's calcaneus (or heel) bone. Belt guide assembly 56 is coupled to sole 25 of surgical boot 10 and is configured to guide main strap assembly 52 toward heel end 30 of sole 25 and up along calf support 26 as shown in FIG. 2. Toothed belt 58 and ratchet 60 cooperate to provide a means for tightening main strap assembly 52 and heel strap assembly 54 around a patient's ankle so that a patient's foot is secured to surgical boot 10. Handle 103 is coupled to ratchet 60 and can be used by a caregiver to locate ratchet 60 by feel or to operate ratchet 60 to tighten main strap assembly 52.

Main strap assembly 52 is situated between toe strap assembly 42 and heel end 30 of sole 25 as shown in FIG. 1. Main strap assembly 52 includes a left strap 55, a right strap 57, a foot pad 101, and a buckle 59 for securing left strap 55 to right strap 57 of main strap assembly 52 over a patient's foot as shown in FIG. 3. Buckle 59 is movable between an open configuration allowing a patient's foot to be lowered into channel 36 of surgical boot 10 and a closed configuration blocking a patient's foot from being lifted out of channel 36 of surgical boot 10. Foot pad 101 is situated between buckle 59 and a patient's foot when main strap assembly 52 extends over the patient's foot as suggested in FIG. 1. Main strap assembly 52 extends through sole 25 of surgical boot 10 and is secured to toothed belt 58 by a fastener 61 as shown in FIGS. 2 and 3.

Heel strap assembly 54 includes a strap 106 and a heel pad 108 as shown in FIG. 3. Strap 106 is coupled at a first end log to left strap 55 of main strap assembly 52 and at a second end 107 to right strap 57 of main strap assembly 52 as suggested in FIG. 3. Heel pad 108 is situated between heel strap 106 and a patient's heel to cushion the patient's heel as suggested in FIG. 2.

Belt guide assembly 56 includes a top plate 63, a bottom plate 65, and a pair of guide pins 67, 69 as shown in FIG. 3. Top plate 63 and bottom plate 65 which guide pins 67, 69 and top plate 63 is coupled to bottom plate 65 by fasteners 86, as shown in FIG. 3. Plates 63, 65 and guide pins 67, 69 cooperate to provide means for redirecting left and right straps 55, 57 of main strap assembly 52 from left and right sides 32, 34 of sole 25 toward heel end 30 of sole 25.

Additional details regarding tightener system 50 are provided in U.S. application Ser. No. 13/151,627 titled "Surgical Boot with Tightener system" which is filed concurrently herewith and which is hereby incorporated by reference.

Calf support 26 includes a left leg 62, a right leg 64, and a calf plate 66 supported above the heel end 30 of sole 25 as shown in FIG. 2. Left leg 62 extends up from left side 32 of sole 25 and supports calf plate 66. Right leg 64 extends up from right side 34 of sole 25 and supports calf plate 66. Left leg 62, right leg 64, and calf plate 66 cooperate to form an opening 68 above the heel end 30 of sole 25 as shown in FIG. 2. Opening 68 is situated between sole 25 and calf plate 66.

Toe strap assembly 42 of foot securing system 38 is configured to extend across a patient's foot near the toe end 28 of sole 25 when a patient is secured to surgical boot 10 as shown, for example, in FIG. 1. Toe strap assembly 42 includes a left strap 70, a right strap 72, a buckle 74, and a toe pad 76 as shown in FIG. 3. Left strap 70 of toe strap assembly 42 has a first end 78 coupled to left side 32 of sole 25 by a fastener 79 and a second end 80. Right strap 72 of toe strap assembly 42 has a first end 82 coupled to right side 34 of sole 25 by a fastener 83 and a second end 84 coupled to buckle 74. Buckle 74 of toe strap assembly 42 is configured to move between an open configuration allowing a patient's foot from being lifted out of channel 36 of surgical boot 10 and a closed configuration blocking a patient from lifting his foot out of channel 36. Buckle 74 is slidably coupled to left strap 70 so that toe strap assembly 42 may be tightened or loosened over a patient's foot by a caregiver. Toe pad 76 is situated between buckle 74 and a patient's foot to cushion a patient's foot when toe strap assembly 42 extends over a patient's foot as shown in FIG. 1.

Leg strap assembly 46 of calf securing system 40 is configured to extend over a patient's lower leg near the top end 37 of calf support 26 when a patient is secured to surgical boot 10 as suggested in FIG. 1. Leg strap assembly 46 includes a left strap 90, a right strap 92, a buckle 94, and a leg pad 96 as shown, for example, in FIG. 3. Left strap 90 of leg strap assembly 46 has a first end 98 coupled to calf plate 66 by a fastener 99 and a second end 100. Right strap 92 of leg strap assembly 46 has a first end 102 coupled to calf plate 66 by a fastener 105 and a second end 104. Buckle 94 of leg strap assembly 46 is configured to move between an open configuration allowing a patient's lower leg to be lowered into channel 36 of surgical boot 10 and a closed configuration blocking a patient's lower leg from being lifted out of channel 36 of surgical boot 10. Buckle 94 is slidably coupled to left strap 90 so that leg strap assembly 46 may be tightened or loosened over a patient's lower leg by a caregiver. Leg pad 96 is situated between buckle 94 and the patient's lower leg to cushion a patient's lower leg when leg strap assembly 46 extends over a patient's lower leg as shown in FIG. 1.

Shell 12 is further formed to include a rear guide beam 110 arranged behind the calf support 26 and a channel 112 for guiding left and right straps 55, 57 of main strap assembly 52 and toothed belt 58 along calf support 26 as shown in FIG. 2. Surgical boot 10 includes a pair of beam guide pins 114 as shown in FIGS. 2 and 3 for holding left and right straps 55, 57 of main strap assembly 52 in position relative to rear guide beam 110. Surgical boot 10 also includes a channel guide pin 118 as shown in FIGS. 2 and 3 for holding left and right straps 55, 57 of main strap assembly 52 in position relative to channel 112 along calf support 26.

In illustrative operation, a caregiver moves buckle 59 of main strap assembly 52, buckle 74 of toe strap assembly 42, and buckle 94 of leg strap assembly 46 to the open position to allow a patient's foot to be lowered into channel 36 of surgical boot 10. A user then lowers a patient's foot into channel 36 of surgical boot 10. Next, a caregiver moves buckle 59 of main strap assembly 52, buckle 74 of toe strap assembly 42, and buckle 94 of leg strap assembly 46 to the closed position to block the patient's foot from being removed from surgical boot 10 as suggested in FIG. 1. Then the caregiver actuates ratchet 60 to move toothed belt 58 thereby tightening main strap assembly 52 and heel strap assembly 54 around a patient's ankle so that a patient's foot is secured to surgical boot 10. The caregiver may then couple quick disconnect receiver 15 with coupler 41 to support surgical boot 10 at a location or for movement along coupler 41. A surgeon or caregiver may then manipulate the position or arrangement of the patient by gripping one or more of the plurality of handles 18, 20, 22, 24. The provision of handles 18, 20, 22, 24 integral to shell 12 of surgical boot 10 allows a caregiver or surgeon to manipulate the position or arrangement of the patient without directly grabbing a patient's foot or lower leg. Surgical boot 10 may be used by a caregiver during hip arthroscopy, fracture procedures, or other operations, for example.

Figure 5:
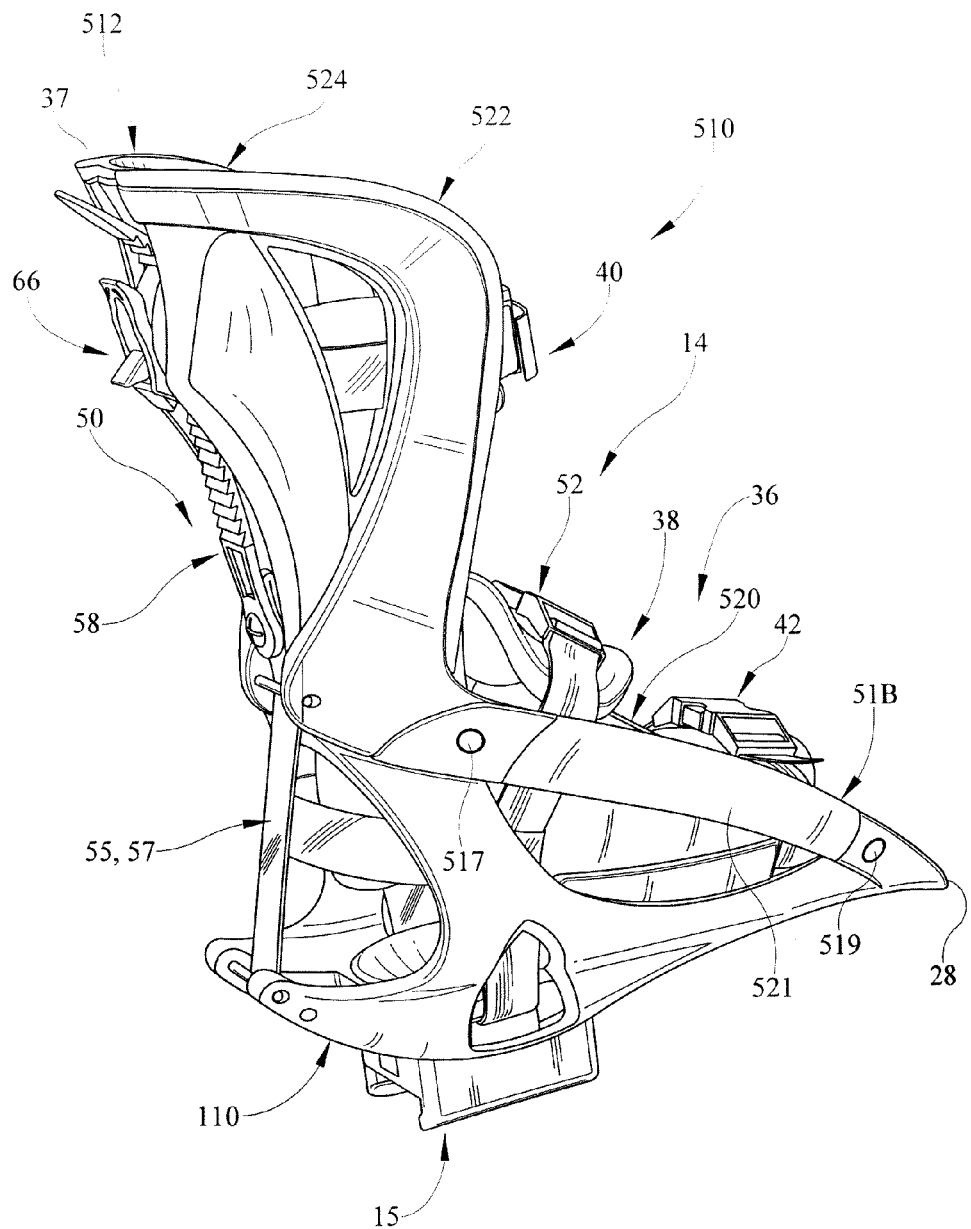
FIG. 5 is a rear perspective view of another surgical boot including a shell and a securing system and showing that a pair of upper handles are formed by the shell and a pair of lower handles are coupled to the shell by fasteners.

Another surgical boot 510 is shown in FIG. 5. Surgical boot 510 is similar to surgical boot 10 shown in FIGS. 1-4 and like reference numerals are used to denote similar parts. However, surgical boot 510 includes a shell 512 providing supporting structure for the surgical boot 510 that differs from shell 12 of surgical boot 10 as described below. The shell 512 includes a main body 516 and a plurality of handles 518, 520, 522, 524 coupled to main body 516.

Plurality of handles 518, 520,5 22, 524 is made up of lower left handle 518, lower right handle 520, upper left handle 522, and upper right handle 524 as suggested in FIG. 5. Lower left and lower right handles 518, 520 are illustratively coupled to main body 516 by fasteners 517, 519 as shown, for example, in FIG. 5. Lower left and lower right handles 518, 520 may be made from a metallic material with a rubberized gripping surface 521 disposed between fasteners 517, 519 as shown in FIG. 5. Upper left and upper right handles 522, 524 are integrally formed with main body 516 of shell 512 from a monolithic plastics material. Illustratively, upper left and upper right handles 522, 524 and main body 516 may be made from an ABS polycarbonate blended material. Further, upper left and upper right handles 522, 524 have a thickness similar to a thickness of main body 516. Illustratively, upper left and upper right handles 522, 524 and the main body 516 have a thickness of about 0.2 inches. In other embodiments, upper left and upper right handles 522, 524 may be coupled to main body 516 by fasteners.

Although certain illustrative embodiments have been described in detail above, variations and modifications exist within the scope and spirit of this disclosure as described and as defined in the following claims.

The invention claimed is:

1. A surgical boot comprising a shell shaped to receive a patient's foot, the shell having a plurality of arcuate handles molded integrally with a main body of the shell, the main body having a sole and a calf support that cooperates with the sole to form an upwardly-facing channel sized to receive a patient's foot and lower leg, the arcuate handles being sized and arranged to extend upwardly away from the sole and outwardly away from the upwardly-facing channel and one another for gripping by a caregiver during surgery to reposition a patient's foot, and a securing system including a foot securing system configured to couple a patient's foot to the shell and a calf securing system configured to couple a patient's leg to the shell, the foot securing system includes a toe strap assembly coupled to the shell and configured to extend over a patient's foot near a toe end of the shell, and the calf securing system includes a calf strap assembly coupled to the shell and configured to extend over a patient's leg near a heel end of the shell, wherein the foot securing system further includes a main strap assembly and a heel strap assembly, the main strap assembly including at least one main strap configured to extend over a patient's foot, and the heel strap assembly including at least one heel strap coupled to the at least one main strap and configured to extend around a patient's heel.

2. The surgical boot of claim 1, wherein the foot securing system further includes a cushion disposed on the heel strap to provide cushioned support to a patient's heel.

3. The surgical boot of claim 1, wherein the plurality of handles form a plurality of handhold openings extending through the shell.

4. The surgical boot of claim 1, wherein the shell has a substantially uniform thickness.

5. The surgical boot of claim 1, wherein the heel strap is configured to extend around a patient's heel between the main body and the upwardly-facing channel.

6. The surgical boot of claim 1, further comprising a guide assembly coupled to the sole and configured to guide the at least one main strap toward the heel end.

7. The surgical boot of claim 6, wherein guide assembly is configured to guide the at least one main strap along the calf support.

8. A surgical boot comprising a shell shaped to receive a patient's foot, the shell having a plurality of arcuate handles molded integrally with a main body of the shell, the main body having a sole and a calf support that cooperates with the sole to form an upwardly-facing channel sized to receive a patient's foot and lower leg, the arcuate handles being sized and arranged to extend outwardly away from the upwardly-facing channel and one another for gripping by a caregiver during surgery to reposition a patient's foot, wherein the surgical boot further comprises a receiver configured to couple the surgical boot to a surgical support, the receiver extends down from the sole of the shell and includes a release handle for disconnection of the surgical boot from the surgical support, wherein the receiver comprises a quick disconnect receiver including a receiver body having a yolk slot defined therein and a retainer lug operable for selective engagement and disengagement by the release handle, and the receiver body includes a yolk slot defined therein, the yolk slot including a first opening and a second opening, the first opening extending through a lower wall of the receiver body orthogonal to the second opening.

9. The surgical boot of claim 8, wherein the plurality of handles form a plurality of handhold openings extending through the shell.

10. The surgical boot of claim 8, wherein the shell has a substantially uniform thickness.

11. The surgical boot of claim 8, wherein the receiver body includes a yolk collar including a ledge defined by the yolk slot, wherein the first opening of the yolk slot has a first lateral width and the second opening has a second width greater than the first lateral width to define the ledge.

12. The surgical boot of claim 11, wherein the retainer lug is arranged within the yolk slot.

13. The surgical boot of claim 8, further comprising a guide assembly coupled to the sole of the shell for directing a number of straps for securing the patient's foot with the shell.

14. The surgical boot of claim 13, wherein the guide assembly is arranged between the yolk slot and the sole.

15. The surgical boot of claim 14, wherein guide assembly includes a top plate, a bottom plate, and a number of guide pins disposed between the top and bottom plate for directing the number of straps.

16. A surgical boot comprising a shell including a sole, a calf support extending above a heel end of the sole, and a first pair of arcuate handles extending between the heel end of the sole and a toe end of the sole and a second pair of handles arranged on opposite lateral sides of the shell and positioned on an end of the calf support opposite the sole, wherein the shell forms an upwardly-facing channel open from the heel end of the sole to the toe end of the sole and the first pair of arcuate handles extend outwardly away from the upwardly-facing channel and one another, wherein the first pair of handles form a first pair of handhold spaces extending through the shell and the second pair of handles form a second pair of handhold spaces extending through the shell, the first and second pairs of handhold spaces configured to receive a user's hand therethrough to grasp around the respective handle.

17. The surgical boot of claim 16, further comprising a securing system including a foot securing system adapted to secure a patient's foot to the sole and a calf securing system adapted to secure a patient's calf to the calf support.

18. The surgical boot of claim 17, wherein the foot securing system includes a toe strap assembly and a main strap assembly, the toe strap assembly coupled to the sole and extending from a right side to a left side of the sole near the toe end of the sole, and the main strap assembly extending from a right side to a left side of the sole between the toe strap assembly and the heel end of the sole.

19. The surgical boot of claim 16, further comprising a coupler configured to couple to a surgical support.

20. A surgical boot comprising
an integrally formed shell including a sole having a toe end and a heel end, a calf support situated above the sole at the heel end of the sole, a first pair of arcuate handles situated above the sole, the first pair of arcuate handles forming a first pair of handhold openings on opposing sides of the shell, and a second pair of handles situated above the sole on an end of the calf support opposite the sole, the second pair of handles forming a second pair of handhold openings on the opposing sides of the shell, the first and second pairs of handhold spaces each configured to receive a user's hand therethrough to grasp around the respective handle
wherein the sole and the calf support cooperate to define an upwardly-facing channel and the first pair of arcuate handles extend outwardly away from the upwardly-facing channel and one another.

21. The surgical boot of claim 20, further comprising a securing system including a foot securing system adapted to secure a patient's foot to the sole and a calf securing system adapted to secure a patient's calf to the calf portion wherein the securing system is situated between the first pair of handles.

22. The surgical boot of claim 20, further comprising a coupler extending down from the sole and configured to couple to a surgical support.

\* \* \* \* \*